Figure 1:
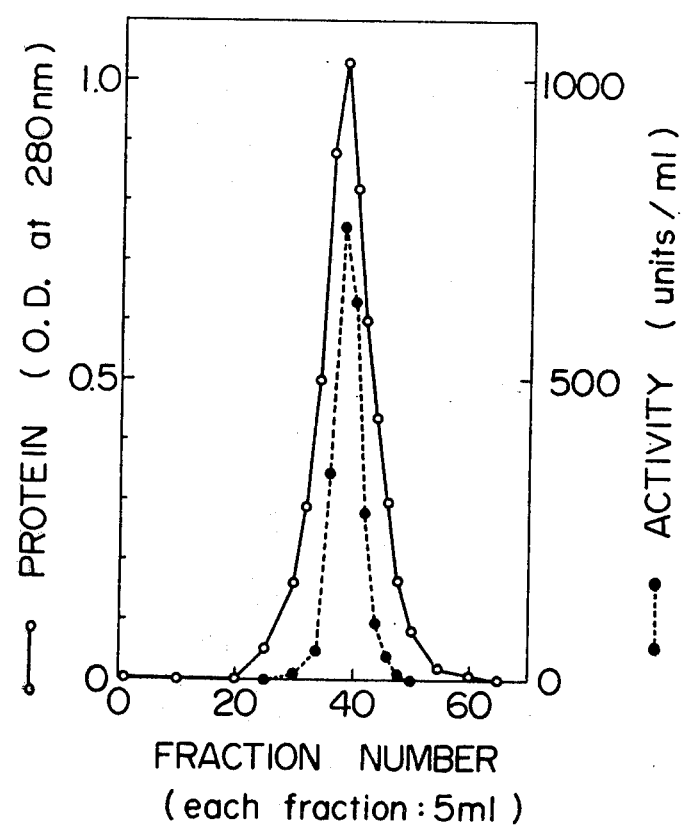

United States Patent [19]

Miura et al.

[11] 4,017,362

[45] Apr. 12, 1977

[54] MICROBIOLOGICAL PROCESS FOR PREPARING L-TARTARIC ACID IN PRESENCE OF SURFACTANTS

[75] Inventors: Yuichi Miura, Tokuyama; Kiyohiko Yutani, Kudamatsu; Hitoshi Takesue, Yamaguchi; Kenji Fujii, Tokuyama, all of Japan

[73] Assignee: Tokuyama Soda Kabushiki Kaisha, Japan

[22] Filed: Feb. 5, 1976

[21] Appl. No.: 655,411

[52] U.S. Cl. .............................. 195/30; 195/66 R
[51] Int. Cl.$^2$ ......................................... C12D 1/02
[58] Field of Search ...................................... 195/30

[56] References Cited

OTHER PUBLICATIONS

Martin et al., Journal of Bacteriology, vol. 70, pp. 405-414 (1955).

*Primary Examiner*—Alvin E. Tanenholtz
*Attorney, Agent, or Firm*—Fitzpatrick, Cella, Harper & Scinto

[57] ABSTRACT

A process for preparing L-tartaric acid, which comprises contacting a microorganism of the genus Nocardia having the ability to produce an enzyme which hydrolyzes the epoxy ring of cis-epoxysuccinic acid, or a crude enzyme isolated therefrom, with cis-epoxysuccinic acid or its derivatives in an aqueous medium in the presence of a surfactant, and recovering the resulting L-tartaric acid.

15 Claims, 5 Drawing Figures

2ND SEPHADEX G-200 GEL FILTRATION

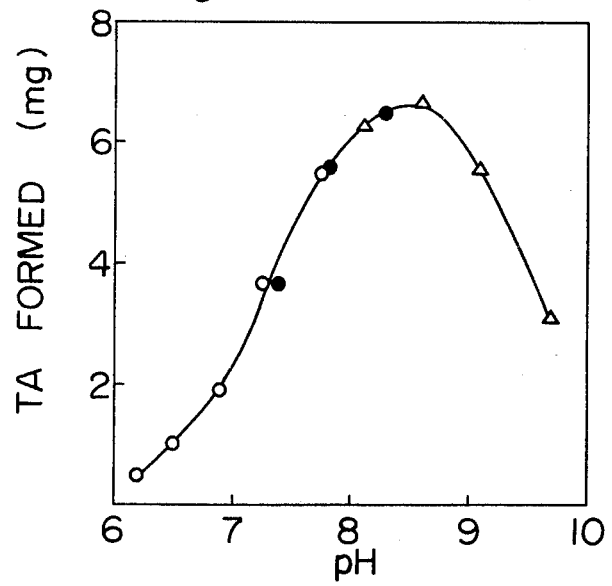
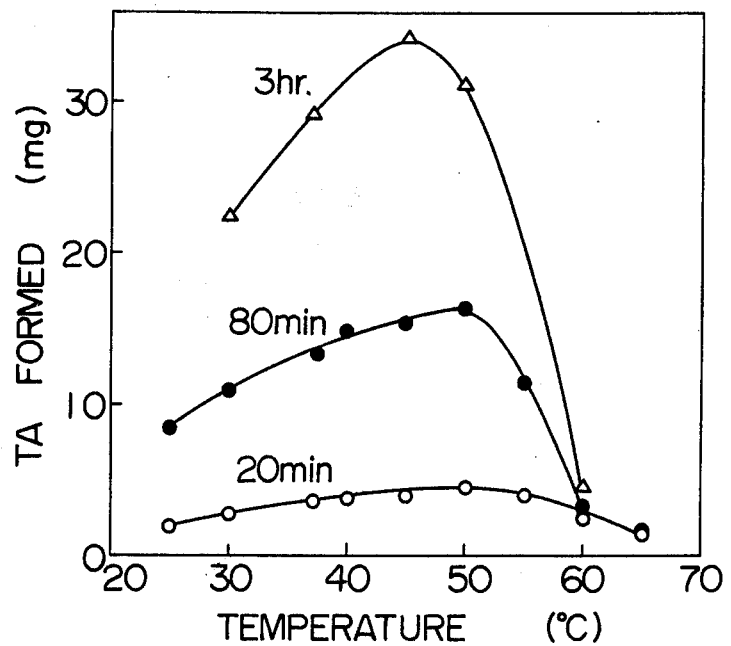

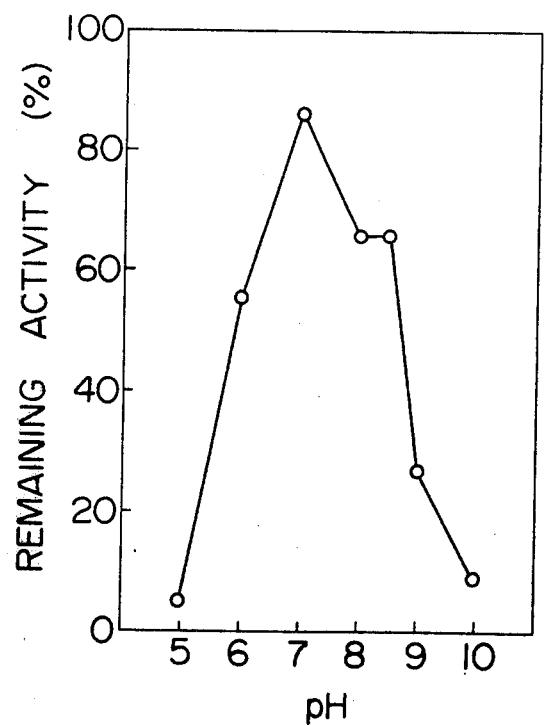
Fig. 4 pH STABILITY
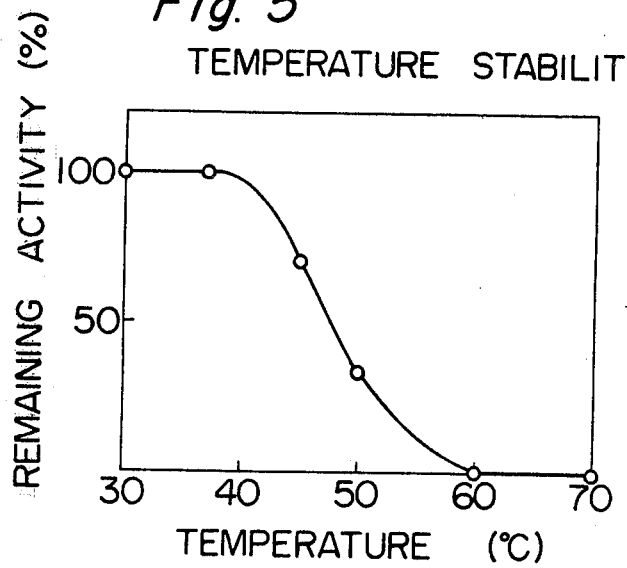
Fig. 5 TEMPERATURE STABILITY

MICROBIOLOGICAL PROCESS FOR PREPARING L-TARTARIC ACID IN PRESENCE OF SURFACTANTS

This invention relates to a process for preparing L-tartaric acid, the same type as naturally occurring tartaric acid, from inexpensive and readily available cisepoxysuccinic acid or its derivatives by an enzymatic technique with commercial advantage. More specifically, the invention relates to a process for preparing L-tartaric acid which comprises contacting a microorganism belonging to the genus Nocardia and having the ability to produce an enzyme which hydrolyzes the epoxy ring of cis-epoxysuccinic acid, or a crude enzyme isolated from said microorganism with cis-epoxysuccinic acid or its derivatives in an aqueous medium in the presence of surfactants, and recovering the resulting L-tartaric acid.

L-tartaric acid, as used in the present application, is a term denoting dextrorotatory (+) tartaric acid which is natural tartaric acid.

Heretofore, L-tartaric acid has been produced by extracting techniques using tartar in wine lees as a raw material. The supply of the raw material has therefore been unstable and restricted, and it has been desired to develop a process which can afford L-tartaric acid from an inexpensive and readily available raw material. In an attempt to meet this demand, methods for synthesizing tartaric acid from maleic acid as a raw material have been developed. The tartaric acid obtained by such methods, however, is a racemic form (DL-form). The DL-form has a defect of exceedingly lower solubility than L-form, and this defect has limited its utilization in many ways. It is very disadvantageous on the other hand, from the viewpoint of operation and cost to convert the Dl-form to an L-form by a complex and disadvantageous optically resolving technique and racemizing technique.

Some suggestions have already been made to produce tartaric acid by a fermentation technique or a technique utilizing microorganisms. For example, United States Patent 2,947,665 discloses that eso-tartric acid can be produced by hydrolyzing trans-epoxysuccinic acid by a technique utilizing a microorganism. However, the U.S. Patent fails to show the production of L-tartaric acid and any technique using microorganisms for the preparation of L-tartaric acid from cis-epoxysuccinic acid. Very recently, a technique for producing L-tartaric acid from cis-epoxy-succinic acid by a technique utilizing microorganisms was suggested (Japanese Laid-Open Patent Publications Nos. 140683/75 and 140684/75 and German OLS 2517941). These patents disclose that microorganisms belonging to the genus Achromobacter or the genus Alcaligenes have the ability to produce an enzyme which is useful for enzymatically converting cis-epoxysuccinic acid to L-tartaric acid (termed "d-tartaric acid" in these patents). However, the patents fail to show anything about microorganims which belong to the genus Nocardia, a quite different genus.

We have discovered the existence of microorganisms of the genus Nocardia which have the ability to produce an enzyme that can enzymatically convert inexpensive and readily available cis-epoxysuccinic acid to L-tartaric acid with superior activity. We have also found that the enzyme which is produced by the microorganisms of the genus Nocardia, for example, *Nocardia tartaricans* nov. sp., and can convert cis-epoxysuccinic acid to L-tartaric acid by hydrolyzing its epoxy ring (which will be referred to as cis-epoxysuccinate hydrolase) is completely different from the enzymes described in the above-cited patents in some of their properties such as the molecular weight, optimum pH or optimum temperature. It has also been found that according to the process of this invention, L-tartaric acid, the same type as natural tartaric acid, can be prepared with commercial advantage in a markedly improved output amounting to about 800 units ($\mu$ moles/hr)/ml. broth or more as a result of contacting a microorganism of the genus Nocardia having the ability to produce cis-epoxysuccinate hydrolase or a crude enzyme isolated from the microorganism with cis-epoxysuccinic acid or its derivatives in an aqueous medium in the presence of a surfactant, preferably a nonionic, anionic or cationic surfactant. The above-mentioned patents which disclose the utilization of microorganisms belonging to the genus Achromobacter or Alcaligenes do not give any description about the utilization of surfactants.

The development of the process of this invention has made it possible to provide L-tartaric acid at lower cost and with greater availability, and therefore, is an important contribution to the field of technology to which the present invention pertains.

Accordingly, it is an object of this invention to provide a process for preparing L-tartaric acid, the same type as natural tartaric acid, with commercial advantage.

Another object of this invention is to provide microorganisms and enzymes produced thereby for utilization in achieving the aforesaid object, and to provide a process which contributes further to the technology of preparing L-tartaric acid.

The above and other objects of this invention along with its advantages will become more apparent from the following description.

The cis-epoxysuccinic acid or its derivatives used in the performance of the process of this invention can be easily obtained, for example, by epoxidizing maleic anhydride, maleic acid or a derivative of any of these with hydrogen peroxide. Examples of the derivatives of cis-epoxysuccinic acid are inorganic salts such as sodium, potassium, calcium and ammonium salts of said acid; organic salts such as primary, secondary and tertiary aliphatic amine, aromatic amine, pyridine and quinoline salts of said acid; and esters or amides such as those formed between said acid and aliphatic alcohols or aromatic alcohols or primary or secondary aliphatic or aromatic amines. Any derivatives can be used which are soluble in the aqueous medium and do not adversely affect the ability of the cis-epoxysuccinate hydrolase to hydrolyze the epoxy ring of cis-epoxysuccinic acid. The cis-epoxysuccinic acid or its derivatives may be in the form of crystals or the reacton mixture as obtained by a synthetic process. However, the presence of impurities in amounts which will retard the reaction, such as too much hydrogen peroxide, is not desirable.

The concentration of the substrate in the process of this invention can be varied over a wide range, usually from 0.1% by weight as initially charged to very high concentrations. When cis-epoxysuccinic acid or its derivative is caused to be present at the time of growing microbial cells in culture media, the growth of the cells tends to be inhibited by too high a concentration of cis-epoxysuccinic acid. Preferably, therefore, the concentration of the cis-epoxysuccinic acid or its derivatives should be adjusted, for example, to not more than about 10%, preferably not more than 5% by weight. Higher concentrations can be employed when the microorganism in accordance with this invention or an L-tartaric acid-forming enzyme isolated therefrom is contacted with cis-epoxysuccinic acid or its derivatives in a system for hydrolyzing the cis-epoxysuccinic acid or its derivatives which is free from the growth of microbial cells.

One preferred species of microorganisms belonging to the genus Nocardia having the ability to produce cis-epoxysuccinate hydrolase is *Nocardia tartaricans* nov. sp. separated from nature. Typical strains of the *Nocardia tartaricans* nov. sp. are deposited in Fermentation Research Institute, Agency of Science and Technology, Japan, and American Type Culture Collection, U.S.A. The characteristics of these strains are described below.

Description of Nocardia tartaricans nov. sp.

(I) Strain ES1-T (FERM P - 2882; ATCC 31191)

A. Morphological characteristics

Rods: $0.8 - 10\ \mu$ by $5 - 30\ \mu$ in young cultures, $0.8 - 1.0\ \mu$ by $1 - 5\ \mu$ in older cultures; in young cultures, mycelium-like development, branching, bending are observed; in older cultures, small rods to coccoids; aerial mycelium is not formed on any tested agar slant; non-motile; not acid-fast; Gram-positive; spore is not formed B. Cultural characteristics 1. Nutrient agar colonies: circular, capitate, smooth, entire, opaque glistening, yellowish-orange to reddish orange
2. Glucose-peptone agar colonies: circular, umbonate, smooth, undulate, opaque, dull, yellowish orange
3. Glycerol-asparagine agar colonies: rhizoid, umbonate, opaque, glistening, pale orange
4. Nutrient broth: slightly turbid, pellicle, sediment
5. Gelatin stab: good growth at surface, no liquefaction
6. Nutrient agar slant: growth abundant, spreading, glistening, butyrous, pale yellowish brown at first, becoming yellowish orange and reddish orange with culture age
7. Sucrose-nitrate agar slant: growth moderate, pale orange, diffusible pigment not formed
8. Glucose-asparagine agar slant: growth moderate, pale orange, diffusible pigment not formed
9. Glycerol-asparagine agar slant: growth moderate, pale orange, diffusible pigment not formed
10. Starch agar slant: growth scanty, colorless, diffusible pigment not formed
11. Tyrosine agar slant: growth moderate, pale orange, diffusible pigment not formed
12. Yeast malt agar slant: growth abundant, orange, diffusible pigment not formed
13. Cat-meal agar slant: growth moderate, pale orange, diffusible pigment not formed
14. Inorganic salts agar slant: growth scanty on inorganic salt agar containing no carbon sources, colorless, diffusible pigment not formed
15. Potato plug: growth abundant, yellowish orange to reddish orange, diffusible pigment not formed C. Physiological characteristics 1. Temperature for growth: 10°– 45° C.
2. Optimum temperature for growth: 25°– 40° C.
3. pH range for growth: 5.5 – 11
4. Salt tolerancy: not inhibited by 10% NaCl
5. Resistant to 0.001% Lysozyme
6. Penicillin sensitive (5 i.u. discs.)
7. Nitrate reduction: positive
8. Voges-Proskauer test: negative
9. Methyl red test: negative
10. Indole production: negative
11. Hydrogen sulfide production: positive
12. Ammonia production from peptone: negative
13. Liquefaction of gelatin: negative
14. Peptonization of casein: negative
15. litmus milk: alkaline, slight clearing with age, no coagulation
16. Hydrolysis of starch: negative
17. Hydrolysis of cellulose: negative
18. Catalase: positive
19. Cytochrome oxidase: negative
20. Urease: positive
21. Hydrolysis of DNA: negative
22. Ammonium salt, nitrate, urea are utilized as source of nitrogen
23. Acetic, n-butyric, lactic, succinic, citric, malic, L-tartaric acids assimilated
24. Cleavage of carbohydrates: Acid without gas from L-arabinose, D-xylose, D-glucose, D-fructose, D-mannose, sucrose, maltose, trehalose, glycerol, ethanol, D-sorbitol, D-mannitol, inositol; neither acid nor gas from galactose, lactose, raffinose, dextrin
25. Assimilation of various carbon sources (incubated on Pridham and Gottlieb agar and broth at 30° C for 3 weeks) L-arabinose (+), D-xylose (+), D-glucose (+), D-fructose (+), sucrose (+), inositol (30), L-rhamnose (+), raffinose (+), D-mannitol (+), ethanol (+), n-propanol (+), isopropanol (+), n-butanol (+), propylene glycol (+), glycerol (+), propylene oxide (+), n-paraffin (+), acetamide (+) phenol (−), p-cresol (−), m-cresol (−), naphthalene (±)

D. Infrared absorption spectra of whole cells

Infrared absorption spectra of whole cells obtained by shaking culture on a glycerol Kelner-Morton medium were studied by Arai's method (J. General Applied microbiology, 9, 119 (1963)).

Key absorption patterns were as follows;

Region I (2800–3000 $cm^{-1}$): type D,
Region II (1650–1750 $cm^{-1}$): type D,
Region III (1370–1550 $cm^{-1}$): type C,
Region IV (950–1250 $cm^{-1}$): type C (II) Strain ES3-T (FERM P - 3304; ATCC 31190)

The organism has a close resemblance to strain ES1-T except for the following characteristics: neither acid nor gas from L-arabinose, D-xylose, D-mannose, maltose Investigation of ES1-T and ES3-T strains by Bergey's Manual of Determinative Bacteriology, eighth edition and Waksmann, The Actinomycetes, Vol. 2 has shown that they are novel species belonging to the genus Nocardia.

*Nocardia vaccinii, Nocardia lutea, Nocardia corallina, Nocardia salmonicolor, Nocardia rubra,* and *Nocardia opaca* can be cited as species analogous to the strains in accordance with this invention. The ES1-T strain and ES3-T strain differ from *Nocardia vaccinii* and *Nocardia lutea* in regard to the growth characteristics on a nutrient agar plate, the formation of mycelium, acid-fastness, fastness, the pH range for growth, and the hydrolyzability of deoxyribonucleic acid (DNA), as shown in Table 1 to be given hereinbelow. Furthermore, as shown in Table 2, these strains differ from *Nocardia corallina* in regard to the growth characteristics on a nutrient agar plate, the optimum growth temperature, tolerancy to NaCl, the formation of acid from sucrose, and the utilizatin of phenol and m-cresol; and from *Nocardia salmonicolor* in regard to the growth characteristics on a nutrient agar plate, the growth characteristics on a glycerol-asparagine agar plate, the optimum growth temperature, the growth pH, tolerancy to NaCl, the formation of acid from dextrin, and the utiization of p-cresol. As shown in Table 3, the ES1-T strain and ES3-T strain further differs from *Nocardia rubra* in regard to the growth characteristics on a nutrient agar plate, the optimum growth temperature, tolerancy to NaCl, and the reducton of nitrate; and from *Nocardia opaca* with regard to the growth characteristics on a nutrient agar plate, the optimum growth temperature, the growth pH and salt resistance. Since ES1-T strain and ES3-T strain grow in an inorganic salt agar culture medium, their microbiological characteristics were compared with those of *Nocardia marina* and *Nocardia atlantica* which can utilize agar as a carbon source. The results shown in Table 4 demonstrate that these strains differ from *Nocardia marina* and *Nocardia atlantica* in regard to the liquefaction of gelation and the decompositon of cellulose.

Table 1

| | | Nocardia tartaricans nov. sp. ES1-T (FERM-P2882; ATCC 31191) ES3-T (FERM-P3374; ATCC 31190) | Nocardia vaccinii | Nocardia lutea |
|---|---|---|---|---|
| 1) | Nutrient agar colonies | yellowish orange to reddish, orange capitate, smooth, entire | reddish, flat, irregular borders | |
| 2) | Aerial mycelium | not formed on any tested agar slant | white | white |
| 3) | Acid fastness | negative | positive | partially positive |
| 4) | Temperature for growth | 10 – 45° C | 10 – 35° C | 10 – 40° C |
| 5) | pH range for growth | 5.5 – 11 | 6 – 9 | 6 – 10 |
| 6) | Hydrolysis of DNA | negative | positive | positive |

Table 2

| | | Nocardia tartaricans nov. sp. ES1-T (FERM-P2882; ATCC 31191) ES3-T (FERM-P3374; ATCC 31190) | Nocardia corallina | Nocardia salmonicolor |
|---|---|---|---|---|
| 1) | Nutrient agar colonies | Same as in Table 1 | coral-red, raised, filamentous or arborescent margins | salmon-pink, raised, rough |
| 2) | Glycerol-asparagine agar colonies | growth moderate, pale orange, rhizoid | | well developed red-orange colonies |
| 3) | Temperature for growth | 10 – 45° C | | 10 – 40° C |
| 4) | Optimum temperature for growth | 25 – 40° C | 25 – 28° C | 28° C. |
| 5) | pH range for growth | 5.5 – 11 | | 5 – 10 |
| 6) | Salt (NaCl) tolerancy | 10% | 7% | 5% |
| 7) | Cleavage of carbohydrate | no acids from dextrin; acid produced from sucrose | no acid from sucrose | acid from dextrin |
| 8) | Assimilation of carbon sources | phenol, m-cresol, p-cresol are not utilized as sole carbon sources | phenol, m-cresol utilized | p-cresol utilized |

Table 3

| | | Nocardia tartaricans nov.sp. ES1-T (FERM-P2882; ATCC 31191) ES3-T (FERM-P3374; ATCC 31190) | Nocardia rubra | Nocardia opaca |
|---|---|---|---|---|
| 1) | Nutrient agar colonies | Same as in Table 1 | bright red, flat, rough, undulate margins | pale buff-pink, raised, rough, filamentous to entire margins |
| 2) | Optimum | | | |

Table 3-continued

|   | | Nocardia tartaricans nov.sp. ES1-T (FERM-P2882; ATCC 31191) ES3-T (FERM-P3374; ATCC 31190) | Nocardia rubra | Nocardia opaca |
|---|---|---|---|---|
|   | temperature for growth | 25 – 40 C° | 25 – 28 C° | 30 C° |
| 3) | pH range for growth | 5.5 – 11 | 6 – 10 | 6 – 9 |
| 4) | Salt (NaCl) tolerancy | 10% | 7% | 7% |
| 5) | Nitrate reduction | positive | negative | positive |

Table 4

|   | | Nocardia tartaricans nov.sp. ES1-T (FERM-P3882; ATCC 31191) ES3-T (FERM-P3374; ATCC 31190) | Nocardia marina | Nocardia atlantica |
|---|---|---|---|---|
| 1) | Nutrient agar colonies | Same as in Table 1 | bright lemon-yellow, flat, smooth, undulate margins | yellow to orange-yellow |
| 2) | Gelatin liquefaction | negative | positive | positive |
| 3) | Nitrate reduction | positive | negative | positive |
| 4) | Hydrolysis of cellulose | negative | positive | positive |
| 5) | Hydrolysis of starch | negative | positive | negative |

On the basis of the above examination, ES1-T strain and ES3-T strai have been identified as novel species belonging to the genus *Nocardia*, and termed *Norcardia tartaricans* nov. sp.

According to the process of this invention, a microorganism of the genus *Nocardia*, preferably *Nocardia tartaricans* nov. sp., having the ability to produce cis-epoxysuccinate hydrolase, or an enzyme isolated from said microorganism is contacted with cis-epoxysuccinic acid or its derivatives in an aqueous medium in the presence of a surfactant.

The cis-epoxysuccinate hydrolase used in this invention is obtained by cultivating the above microorganism in a customary manner. The cultivation of the above microorganism is carried out usually in an aqueous medium. It can also be carried out on a solid surface. Natural culture media such as nutrient broth and synthetic culture media composed of a sutable carbon source such as glucose, sucrose, glycerol, ethanol, isopropanol or n-paraffin, a suitable nitrogen source such as ammonium salts, nitric acid salts and urea and other inorganic salts can be used for the cultivation. It is desirable to add cis-epoxysuccinic acid or its derivatives to the culture medium for inducing the required enzyme.

The pH of the culture medium is adjusted to 5.5 to 11, preferably about 6 – 10. The cultivation is carried out aerobically at about 10 to about 45° C, preferably about 25 to about 40° C. In batchwise operations, the cultivation is carried out usually for half a day to 10 days.

In the performance of the process of this invention, the contacting of the microorganism having the ability to produce cis-epoxysuccinate hydrolase or an enzyme isolated therefrom with cis-epoxysuccinic acid or its derivative can be effected in various modes. For example, the contacting can be carried out while the microorganism is in the form of growing culture, culture broth, living cells, dried cells, pulverized cells or cell extract. It can also be in the form of purified enzyme by employing a purifying means.

When the enzyme is used in a purified form, the following procedure can be applied to the isolation and purification of the enzyme. Cells harvested from a culture broth by centrifugation are suspended in a 0.05 M phosphate buffer (pH 7) and destroyed by sonic oscillation. The crude cell-free extract thus obtained is fractionated by precipitation with ammonium sulfate and a fraction of 50 to 60% saturation is collected. The precipitate is dissolved in a small volume of 0.05 M phosphate buffer (pH 7) and dialyzed against a large volume of the same buffer and then purified by DEAE-Sephadex A-50 column chromatography and gel filtration with a Sephadex G-200 column.

cis-Epoxysuccinate hydrolase isolated from *Nocardia tartaricans* nov. sp. ES3-T (FERM P-3374; ATCC 31190) and purified by the procedure described above has the following properties. (The elution pattern of the 2nd gel filtration of Sephadex G-200 is shown in FIG. 1.)

1. Catalytic action: hydrolyzes cis-epoxysuccinate, producing L(+)-tartaric acid.

2. Molecular weight: 60,000 – 95,000 by the Andrews method.

3. Substrate specificity: does not hydrolyze d- or ε-trans-epoxysuccinate. 4. Optimum ph: 8 – 9

5. Optimum temperature: 50° C in 20 – 80 minutes' incubation, and 45° C in several hours' incubation 6. pH stability: stable at pH 7.0, unstable at pH below 5.0 and pH over 10.0.

7. Temperature stability: stable at temperatures below 40° C in 10-minute incubation at pH 7.0; lost activity at temperatures higher than 60° C in 10-minute incubation at pH 7.0.

8. Inhibitors and activators: summarized in Table 5 below

Table 5

| Inhibitors and activators | mM | Remaining activity (%) |
|---|---|---|
| None | — | 100 |
| EDTA | 1 | 88 |
|  | 10 | 84 |
| α,α'-Dipyridyl | 1 | 88 |
| o-Phenanthroline | 1 | 39 |
| Ammonium oxalate | 1 | 45 |
| Mercaptoethanol | 10 | 109 |
| p-Chloromercuribenzoate | 1 | 89 |
| Iodoacetamide | 1 | 86 |
| $MgSO_4 \cdot 7H_2O$ | 1 | 106 |
| $FeSO_4 \cdot 4H_2O$ | 1 | 115 |
| $ZnSO_4 \cdot 7H_2O$ | 1 | 55 |
| $CuCl_2 \cdot 2H_2O$ | 1 | 56 |
| $NiCl_2$ | 1 | 86 |
| $CoCl_2$ | 1 | 56 |
| $CaCl_2 \cdot 2H_2O$ | 1 | 111 |
| Fumarate | 10 | 90 |
| dl-trans-Epoxysuccinate | 100 | 126 |

The optimum pH (4), the optimum temperature (5), the pH stability (6), and the temperature stability (7) above are shown in FIGS. 2, 3, 4 and 5. In these FIGS., TA is an abbreviation for L-tartaric acid, and ESA, for cis-epoxysuccinic acid.

The enzymatic activity, the quantity of tartaric acid and the quantity of protein employed in the determination of the enzymatic properties of cis-epoxysuccinate hydrolase used in this invention were measured by the following methods.

1. Measurement of enzymatic activity 1.0 ml of 1M $ESA \cdot Na_2$ was added to 3.9 ml of a 0.1M phosphate buffer (pH 8.0), and the mixture was maintained at 37° C for 5 minutes. Then, 0.1 ml of an enzyme solution was added, and the mixture allowed to stand for 20 minutes at 37° C. The quantity of tartaric acid formed in the resulting reaction mixture was determined. The amount of the enzyme which forms 1 μmole of tartaric acid per hour under the above-mentioned reaction conditions is defined as one unit, and the number of such units per mg of protein is defined as specific activity.

2. Determination of the quantity of tartaric acid

An enzyme reaction solution was added to 1 ml of 2% ammonium metavanadate reagent, and the mixture was diluted to 4 ml with water. Then, 1 ml of 1N sulfuric acid was added, and after a lapse of 30 minutes, the absorbance of the solution at 530 nm was measured.

3. Determination of the quantity of protein

The quantity of protein was determined from the absorbance at 280 nm, setting $E_1^{1\%}{}_{cm}$ at 15.

The cis-epoxysuccinate hydrolase in accordance with this invention differs from the conventional enzymes disclosed in Japanese Laid-Open Patent Publication No. 140684/75 and others cited above which are produced by microorganisms belonging to the genus *Achromobacter* or *Alcaligenes* used to produce L-tartaric acid from cis-epoxysuccinic acid. For example, the prior patent states that the conventional enzymes have a molecular weight of about 25,000 to about 45,000. But this cis-epoxysuccinate hydrolase in accordance with this invention has a molecular weight of about 60,000 to about 95,000. Furthermore, while the optimum pH for the conventional enzymes is 7 to 8, it is 8 to 9 with the cis-epoxysuccinate hydrolase of this invention. The optimum temperature is 57° C for 1-hour incubation and 50 to 52° C for 3-hour incubation for the conventional enzymes, but 50° C for 1-hour incubation and 45° C for 3-hour incubation for the cis-epoxysuccinate hydrolase of this invention.

It is essential that according to the process of this invention, a microorganism having the ability to produce the cis-epoxysuccinate hydrolase or a crude enzyme isolated therefrom is contacted with cis-epoxysuccinic acid or its derivatives in an aqueous medium in the presence of a surfactant, preferably one selected from the group consisting of nonionic, anionic and cationic surfactants. The surfactants can be used either alone or in combination of two or more.

Examples of suitable anionic surfactants are alkyl-polyoxyethylene phosphoric acid esters in which preferably, the alkyl group contains 2 to 20 carbon atoms and the polyoxyethylene has a degree of polymerization of 2 to 20. such as dipolyoxyethylene alkyl ether phosphoric acid ester DDP-8 (made by Nikko Chemicals) and dipolyoxyethylene oleyl ether phosphoric acid ester DOP-8 (made by Nikko Chemicals); and higher fatty acid salts preferably containing 10 to 30 carbon atoms, such as sodium laurate or sodium oleate.

Examples of sutable nonionic surfactants are polyoxyethylene sorbitan fatty acid esters in which preferably, the polyoxyethylene has a degree of polymerizaton of 2 to 50 and the fatty acid moiety contains 2 to 20 carbon atoms, such as polyoxyethylene sorbitan monooleate Tween-80 (made by Kao-Atlas Company); a polyoxyethylene/polyoxypropylene block copolymer such as Pluronic L-61 (made by Nikko Chemicals); and polyoxyethylene alkyl ethers in which preferably, the alkyl group contains 2 to 20 carbon atoms and the polyoxyethylene has a degree of polymerization of 2 to 50, such as polyoxyethylene lauryl ether LB-4.2 and BL-9EX (made by Nikko Chemicals), polyoxyethylene cetyl ether BC-10TX (made by Nikko Chemicals), and polyoxyethylene oleyl ether BO-10TX (made by Nikko Chemicals).

Examples of suitable cationic surfactants are long-chain alkyl quaternary ammonium salts in which preferably, the long-chain alkyl group contains 10 to 30 carbon atoms, such as cetyltrimethyl ammonium bromide; and long-chain alkyl pyridinium salts in which preferably, the long-chain alkyl group contains 10 to 30 carbon atoms, such as lauryl pyridinium chloride.

Trypolyoxy ethylene alkyl ether phosphoric acid ester TDP-8 (made by Nikko Chemicals), polyoxyethylene sorbitan monolaurate Tween-20 (made by Kao-Atlas Company) and polyoxyethylene trioleate Tween-85 (made by Kao-Atlas Company) can also be used in the present invention.

The amount of the surfactant can be optionally changed according to its type, but generally, it is about 1 to about 0.001% by weight based on the aqueous medium.

It is not clear by what mechanism the presence of the surfactant increases the rate of hydrolyzation (hydration) of cis-epoxysuccinic acid or its derivatives to L-tartaric acid by the cis-epoxysuccinate hydrolase and thus increases the amount of L-tartaric acid produced. However, as will be shown in specific working examples to be given hereinbelow, its effect of promoting the formation of L-tartaric acid is striking.

Our investigations show that in the case of the enzymes produced by the microorganism disclosed in the above-cited Japanese Laid-Open Patent Publication No. 140684/75 and others, the addition of surfactants does not appreciably produce a promoting effect in cell suspension reaction. The experiments we conducted in this regard are partly shown below.

Using each of *Achromobacter tartarogenese* nov. sp. TORAY 1246 (FERM P2507), *Achromobacter acinus* nov. sp. TORAY 1366 (FERM P2509) and *Alcaligenes epoxylyticus* nov. sp. TORAY 1128 (FERM P2511) which are disclosed in the above-cited prior patents and *Nocardia tartaricans* nov. sp. ES3-T (FERM P-3374; ATCC 31190) in accordance with the present invention, cis-epoxysuccinic acid is converted to L-tartaric acid (TA) under the same conditions by the same technique in the presence of polyoxyethylene alkyl ether (BL-9EX) as a nonionic surfactant, alkylpolyoxyethylene phosphoric acid ester (DDP-8) as an anionic surfactant, and toluene respectively. The results are shown in Table 6.

L-tartaric acid can be recovered from the reaction mixture, for example, by removing the cells by centrifugal separation and concentrating the filtrate. Another recovering procedure comprises adding a calcium salt to precipitate the product as calcium tartrate tetrahydrate, separating the L-tartarate by filtration or any other desired solid-liquid separating means, and converting it to L-tartaric acid in a conventional manner. The resulting L-tartaric acid has been identified as the same as natural tartaric acid by its Rf value in paperchromatograhpy, its degree of migration in filter paper electrophoresis and also its IR spectrum, NMR spectrum, degree of rotation and elemental analysis values.

The following Examples illustrate the present invention in greater detail.

EXAMPLE 1

50 ml. of a culture medium of the following composition was placed into each of 500 ml. shaking flasks.

| | | |
|---|---|---|
| Propylene glycol | 1 | % |
| $NH_2CONH_2$ | 0.3 | % |
| $KH_2PO_4$ | 0.15 | % |
| $Na_2HPO_4$ | 0.15 | % |
| $MgSO_4 \cdot 7H_2O$ | 0.05 | % |
| $FeSO_4 \cdot 7H_2O$ | 0.001 | % |
| $CaCl_2 \cdot 2H_2O$ | 0.001 | % |
| $MnSO_4 \cdot 4H_2O$ | 0.0002 | % |
| Yeast extract | 0.02 | % |
| pH | 7.0 | |

Table 6

| Microorganisms | Additives | TA (g/l) 10 hours | TA (g/l) 20 hours | Units/ml-broth ($\mu$moles/hr. ml-broth) |
|---|---|---|---|---|
| Achromobacter tartarogenes (FERM P-2507) | — | 17 | 34 | 22.7 |
| | BL-9EX | 15.3 | 29 | 20.4 |
| | DDP-8 | 18 | 36.2 | 24.0 |
| | Toluene 2$\mu$ | 18 | 36.2 | 24.0 |
| Achromobacter acinus (FERM P-2509) | — | 21 | 43 | 28.0 |
| | BL-9EX | 19 | 37 | 25.3 |
| | DDP-8 | 19.5 | 38.8 | 26.0 |
| | Toluene 2$\mu$ | 19.5 | 38.8 | 26.0 |
| Alcaligenes epoxylyticus (FERM P-2511) | — | 23.2 | 43.4 | 30.9 |
| | BL-9EX | 11 | 13.5 | 14.7 |
| | DDP-8 | 23 | 44 | 30.7 |
| | Toluene 2$\mu$ | 22.3 | 44.5 | 29.7 |
| Nocardia tartaricans ES3-T (FERM P-3374: ATCC 31190) | — | 14 | 29 | 18.7 |
| | BL-9EX | 116 | 150 (100%) | 154.6 |
| | DDP-8 | 20 | 42 | 26.7 |
| | Toluene 2$\mu$ | 0 | 0 | 0 |

The reaction can be carried out by a batch method, a continuous method, or a semi-batch method in which the substrate and other required materials are successively fed during the reaction. It is also possible to employ a flow reaction technique in which the microorganism or the enzyme is fixed to a suitable support and packed in a column. The reaction can be carried out at a temperature of about 20° to about 60° C., preferably about 25 to about 45° C at a pH of about 5 to about 10, preferably about 6 to about 10, more preferably about 7 to about 9.

In one embodiment of this invention, cis-epoxysuccinic acid or its derivative can be added either partly or wholly to the liquid culture medium, and then the abovespecified microorganism cultivated in it to build up L-tartaric acid in the culture broth.

The above culture medium was prepared as follows: A culture medium containing the above ingredients except urea was sterilized at 121° C for 15 minutes, and a separately prepared urea solution filtered and sterilized was added. The pH of the mixture was adjusted with sodium hydroxide to afford the culture medium finally having the above-mentioned composition and pH.

One platinum loopful of *Nocardia tartaricans* nov. sp. (strain ES1-T: FERM P-2882: ATCC 31191) was inoculated in the resulting culture medium, and incubated at 30° C for 100 hours. The final cell concentration reached 4.8 g/l. The resulting cells were collected by centrifugal separation, and suspended in a culture medium of the same composition as above except that propylene glycol was omitted and sodium cis-epoxysuccinate was added in a concentration of 0.2 mol/liter. The mixture was maintained at 30° C for 20 hours to induce an enzyme. The cells were again collected by centrifugal separation, and added in a concentration of 5 g/l as dry cells to 10 ml. of a 0.7 mol/l solution of sodium cis-epoxysuccinate (pH 7.0), and then each of the surfactants shown in Table 7 was added in the concentrations indicated. The reaction was carried out at 37° C with shaking. Five hours later, the quantity of the resulting L-tartaric acid was determined. The results are shown in Table 7. It can be seen that the addition of the surfactants markedly accelerated the rate of reaction.

Table 7

| | Concentration (wt. %) | L-Tartaric acid formed (g/l) | Average enzymatic activity (units/mg-cells) |
|---|---|---|---|
| Not added | — | 10.8 | 2.88 |
| Alkyl polyoxyethylene phosphoric acid esters (DDP-8) | 0.1 | 34.4 | 9.17 |
| | 0.05 | 44.0 | 11.7 |
| | 0.025 | 64.0 | 17.1 |
| | 0.0125 | 48.0 | 12.8 |
| Sodium laurate | 0.1 | 8.0 | 2.13 |
| | 0.05 | 12.4 | 3.31 |
| | 0.025 | 22.4 | 5.97 |
| | 0.0125 | 11.2 | 2.99 |
| Cetyltrimethyl ammonium bromide | 0.1 | 10.4 | 2.77 |
| | 0.05 | 8.0 | 2.13 |
| | 0.025 | 84.4 | 22.5 |
| | 0.0125 | 28.0 | 7.47 |
| Lauryl pyridinium chloride | 0.1 | 62.8 | 16.7 |
| | 0.05 | 58.4 | 15.6 |
| | 0.025 | 55.2 | 14.7 |
| | 0.0125 | 57.4 | 15.3 |
| Polyoxyethylene sorbitan fatty acid ester (Tween-80) | 0.1 | 22.4 | 5.97 |
| | 0.05 | 21.2 | 5.63 |
| | 0.025 | 20.8 | 5.55 |
| | 0.0125 | 21.6 | 5.76 |
| Polyoxyethylene/polyoxypropylene block copolymer (Pluronic L-61) | 0.1 | 19.6 | 5.23 |
| | 0.05 | 21.2 | 5.65 |
| | 0.025 | 26.0 | 6.93 |
| | 0.0125 | 36.0 | 9.60 |

EXAMPLE 2

| Propylene glycol | 1 % |
|---|---|
| Urea | 0.3 % |
| $KH_2PO_4$ | 0.2 % |
| $Na_2HPO_4$ | 0.2 % |
| $MgSO_4 \cdot 7H_2O$ | 0.1 % |
| $FeSO_4 \cdot 7H_2O$ | 0.001 % |
| $CaCl_2 \cdot 2H_2O$ | 0.003 % |
| $MnSO_4 \cdot 4H_2O$ | 0.0004 % |
| Yeast extract | 0.02 % |
| pH | 7.0 |

A culture medium containing the above ingredients except urea was sterilized at 121° C for 15 minutes, and a separately prepared urea solution filtered and sterilized was added. The pH of the mixture was adjusted with sodium hydroxide to afford the culture medium finally having the above-mentioned composition and pH.

50 ml. of the culture medium was charged into each of 500 ml. shaking flasks. One loopful of *Nocardia tartaricans* nov. sp. (strain Es1-T: FERM P-2882; ATCC 31191) was inoculated, and cultivated at 30° C for 75 hours.

Separately, a 10-liter jar fermentor was charged with 5 liters of a sterilized culture medium having the same composition as above and 0.1% of Pluronic L-61 (made by Nikko Chemicals) was added as a defoamer. Then, 5 flasks of the culture broth were inoculated and cultivated at 30° C. while passing air at a rate of 5 liters/min. and adjusting the speed of stirring to 600 rpm. The cultivation was continued for 17 hours and when the cell concentration became 0.9 g/l, 100 ml. of a 25% solution of sodium cis-epoxysuccinate (pH 7.0) filtered and sterilized was added in order to induce an enzyme. The cultivation was further continued for 24 hours, and the final cell concentration became 4.73 g/l.

Each of the surfactants shown in Table 8 was added in the concentrations indicated in Table 8 to 10 ml. of the resulting culture broth, and further, 10 ml. of a 1.4 mol/l solution of sodium cis-epoxysuccinate (pH 8.0). Then, the reaction was carried out at 37° C with shaking. Five hours later, the quantity of the resulting L-tartaric acid was determined. The results are shown in Table 8. The addition of the surfactant markedly accelerated the rate of reaction.

Table 8

| Surfactants | Concentration (wt. %) | Tartaric acid formed (g/l) | Average enzymatic activity* (g of tartaric acid/g of cell hr*) | (units/ml-broth) |
|---|---|---|---|---|
| Not added | — | 6.48 | 1.10 | 34.7 |
| Alkyl polyoxyethylene phosphoric acid ester (DDP-8) | 0.1 | 20.6 | 3.48 | 110 |
| | 0.05 | 26.4 | 4.46 | 141 |
| | 0.025 | 38.4 | 6.49 | 205 |
| | 0.0125 | 28.8 | 4.87 | 154 |
| Sodium laurate | 0.1 | 4.8 | 0.81 | 25.5 |
| | 0.05 | 7.4 | 1.25 | 39.4 |
| | 0.025 | 13.4 | 2.26 | 71.3 |
| | 0.0125 | 6.7 | 1.13 | 35.6 |
| Cetyltrimethyl ammonium bromide | 0.1 | 6.2 | 1.05 | 33.1 |
| | 0.05 | 4.8 | 0.81 | 25.5 |
| | 0.025 | 50.6 | 8.55 | 270 |
| | 0.125 | 16.8 | 2.84 | 89.6 |
| Lauryl pyridinium chloride | 0.1 | 37.7 | 6.37 | 201 |
| | 0.05 | 35.0 | 5.92 | 187 |
| | 0.025 | 33.1 | 5.59 | 176 |
| | 0.125 | 34.3 | 5.80 | 183 |
| Polyoxyethylene sorbitan fatty acid ester (Tween-80) | 0.1 | 13.4 | 2.26 | 71.3 |
| | 0.05 | 12.7 | 2.15 | 67.8 |
| | 0.025 | 12.5 | 2.11 | 66.5 |
| | 0.0125 | 13.0 | 2.20 | 69.4 |
| Polyoxyethylene/polyoxypropylene block copolymer (Pluronic L-61) | 0.1 | 11.8 | 1.99 | 62.8 |
| | 0.05 | 12.7 | 2.15 | 68.1 |
| | 0.025 | 15.6 | 2.64 | 83.2 |
| | 0.125 | 21.6 | 3.65 | 115 |
| Polyoxyethylene alkyl ether (BL-9EX) | 0.1 | 71.7 | 12.12 | 382 |
| | 0.05 | 60.3 | 10.19 | 321 |
| | 0.025 | 53.6 | 9.06 | 286 |
| | 0.0125 | 51.8 | 8.75 | 276 |

*The enzymatic activity per ml. of the culture broth over a period of 5 hours.

EXAMPLE 3

| Propylene glycol | 1 | % |
|---|---|---|
| $NH_2CONH_2$ | 0.3 | % |
| $KH_2PO_4$ | 0.15 | % |
| $Na_2HPO_4$ | 0.15 | % |
| $MgSO_4 \cdot 7H_2O$ | 0.05 | % |
| $FeSO_4 \cdot 7H_2O$ | 0.001 | % |
| $CaCl_2 \cdot 2H_2O$ | 0.001 | % |
| $MnSO_4 \cdot 4H_2O$ | 0.0002 | % |
| Yeast extract | 0.02 | % |
| pH | 7.0 | |

A culture medium containing the above ingredients except urea was sterilized at 121° C for 15 minutes, and a separately prepared urea solution filtered and sterilized was added. The pH of the mixture was adjusted with sodium hydroxide to afford a culture medium finally having the above-mentioned composition and pH.

50 ml. of the culture medium as charged into each of 500 ml. shaking flasks. One loopful of *Nocardia tartaricans* nov. sp. (strain ES1-T: FERM P-2882; ATCC 31191) was inoculated in the culture medium, and incubated at 30° C for 100 hours.

After the cultivation, the cells were collected by centrifugal separation, and suspended in a concentration of 5 g/l as dry cells to a culture medium having the same composition as above except that propylene glycol was omitted, and sodium cis-epoxysuccinate was added in a concentration of 0.2 mol/l. The suspension was maintained at 30° C for 20 hours to induce an enzyme. The cells were again collected by centrifugal separation, and suspended in a concentration of 10 g/l as dry cells in 10 ml. of a 0.7 mol/l solution of sodium cis-epoxysuccinate. The suspension was cooled to 0°–5° C, and subjected to an ultrasonic oscillation treatment (20 KHz, 60 W, 10 minutes).

After the ultrasonic oscillation treatment, the cell debris was removed, and to the supernatant liquid was added each of the surfactants shown in Table 9 in the concentrations indicated in Table 9. The addition of the surfactants markedly accelerated the rate of reaction.

Table 9

| Surfactants | Concentration (wt.%) | L-tartaric acid formed (g/l) |
|---|---|---|
| Not added | — | 12.0 |
| | 0.1 | 12.5 |
| | 0.05 | 13.2 |
| Sodium laurate | | |
| | 0.025 | 13.8 |
| | 0.0125 | 20.5 |
| | 0.1 | 49.6 |
| Alkyl polyoxyethylene/phosphoric acid ester (DDP-8) | 0.05 | 52.0 |
| | 0.025 | 54.0 |
| | 0.0125 | 28.0 |
| Alkylphosphoric acid ester sodium salt (SLP, a product of Nikko Chemicals) | 0.1 | 13.2 |
| | 0.05 | 15.5 |
| | 0.025 | 20.8 |
| | 0.0125 | 22.0 |
| | 0.1 | 46.8 |
| Polyoxyethylene sorbitan | | |
| | 0.05 | 48.0 |
| fatty acid ester | | |
| | 0.025 | 47.2 |
| (Tween-80) | | |
| | 0.0125 | 25.6 |
| | 0.1 | 42.4 |
| Polyoxyethylene/polyoxypropyleneblock copolymer | 0.05 | 21.2 |
| | 0.025 | 16.0 |
| (Pluronic L-61) | | |
| | 0.0125 | 14.8 |
| | 0.1 | 42.5 |
| Polyoxyethylene alkyl ether (BL-4.2) | 0.05 | 40.5 |
| | 0.025 | 40.0 |
| | 0.0125 | 39.7 |

EXAMPLE 4

| | | |
|---|---|---|
| Propylene glycol | 1 | % |
| Ammonium sulfate | 0.3 | % |
| KH$_2$PO$_4$ | 0.2 | % |
| Na$_2$HPO$_4$ | 0.2 | % |
| MgSO$_4$ . 7H$_2$O | 0.1 | % |
| FeSO$_4$ . 7H$_2$O | 0.001 | % |
| CaCl$_2$ . 2H$_2$O | 0.003 | % |
| MnSO$_4$ . 4H$_2$O | 0.0004 | % |
| Yeast extract | 0.02 | % |
| pH | 7.0 | |

A culture medium of the above composition was sterilized at 121° C for 15 minutes, and 50 ml. of it was charged into each of 500 ml. shaking flasks. One loopful of *Nocardia tartaricans* nov. sp. (Strain ES3-T: FERM P3374; ATCC 31190) was inoculated in the culture medium, and cultivated at 30° C for 24 hours. Then, filtered and sterilized sodium cis-epoxysuccinate was added to a concentration of 0.6%. When the cultivation was carried out for an additional 24 hours, the cell concentration became 6.93 g/l.

Separately, a 10-liter jar fermentor was charged with 5 liters of a culture medium having the same composition as above which had been sterilized at 121° C for 15 minutes, and 0.1% of Pluronic L-61 was added as a defoamer. Five flasks of the above culture broth were inoculated, and incubated at 30° C while passing air at a rate of 5 liters/min. and adjusting the speed of stirring to 600 rpm. When the cultivation was continued for 7 hours and the cell concentration reached 1.15 g/l, a separately prepared solution of sodium cis-epoxysuccinate filtered and sterilized was added to a concentration of 1.0%. The cultivation was continued for an additional 20.5 inches. The final cell concentration was 4.4 g/l.

Each of the surfactant shown in Table 10 was added to 10 ml. of the culture broth in the concentrations indicated in Table 10. 10 ml. of a 2 mol/l solution of sodium cis-epoxysuccinate (pH 8.0) was further added, and the reaction was carried out at 37° C with shaking. 2.5 Hours later, the quantity of the formed L(+)-. . . . tartaric acid was determined. The results are shown in Table 10. The addition of the surfactants showed a marked effect of accelerating the rate of reaction.

Table 10

| Surfactants | Concentration (wt. %) | L-tartaric acid formed (mg) | Average enzymatic activity (units/ml-broth) |
|---|---|---|---|
| Not added | — | 275 | 73.3 |
| Alkyl polyoxyethylene phosphoric acid ester (DDP-8) | 0.1 | 1155 | 308 |
| | 0.05 | 1397 | 373 |
| | 0.025 | 2024 | 540 |
| | 0.0125 | 1705 | 455 |
| Sodium laurate | 0.1 | 528 | 141 |
| | 0.05 | 990 | 264 |
| | 0.025 | 1122 | 299 |
| | 0.0125 | 935 | 249 |
| Cetyltrimethyl ammonium bromide | 0.1 | 275 | 73.3 |
| | 0.05 | 220 | 58.7 |
| | 0.025 | 1672 | 446 |
| | 0.0125 | 1430 | 381 |
| Lauryl pyridinium chloride | 0.1 | 1804 | 481 |
| | 0.05 | 1694 | 452 |
| | 0.025 | 1683 | 449 |
| | 0.0125 | 1694 | 452 |
| Polyoxyethylene sorbitan fatty acid ester (Tween-80) | 0.1 | 1111 | 296 |
| | 0.05 | 1122 | 299 |
| | 0.025 | 1155 | 308 |
| | 0.0125 | 1144 | 305 |
| Polyoxyethylene/polyoxypropylene block copolymer (Pluronic L-61) | 0.1 | 880 | 235 |
| | 0.05 | 902 | 241 |
| | 0.025 | 946 | 252 |
| | 0.0125 | 1397 | 373 |
| Polyoxyethylene alkyl ether (BL-9EX) | 0.1 | 2915 | 777 |
| | 0.05 | 2508 | 669 |
| | 0.025 | 1727 | 461 |
| | 0.0125 | 1408 | 375 |

EXAMPLE 5

A 10-liter jar fermentor was charged with 5 liters of a culture medium having the same composition as in Example 1, and 0.1% of Pluronic L-61 was added. *Nocardia tartaricans* nov. sp. (strain ES3-T: FERM P-3374: ATCC 31190) was inoculated in the culture medium, and cultivated at 30° C while passing air at a rate of 5 liters/min. and adjusting the speed of stirring to 600 rpm. When the cell concentration reached about 1.0 g/l, sodium cis-epoxysuccinate was added to a concentration of 0.5% by weight. When the cultivation was carried out for 35 hours, the cell concentration reached 4.6 g/l.

The enzymatic activity of this culture broth was determined by the following method.

5 ml. of a mixture consisting of 1.0 ml of the culture broth, 2.9 ml of a phosphate buffer having a pH of 8, 0.1 ml of 5% BL-4.2 and 1.0 ml of 1mol/l sodium cis-epoxysuccinate was reacted with shaking at 37° C for 1 hour, and the quantity of the resulting tartaric acid was determined.

The enzymatic activity per ml of the culture broth, as determined by this method, was 613 units.

4 liters of this culture broth was transferred into a separate 20-liter reactor, and 4 liters of a 1 mol/l solution of sodium cis-epoxysuccinate was added, and reacted at 37° C with stirring, 2 mol/l of sodium cis-succinate was successively added as the sodium cis-epoxysuccinate was consumed. The total amount of the 2 mol/l cis-epoxysuccinate added was 8 liters. At the end of 20 hours, the concentration of L-tartaric acid in the reaction mixture became 184 g/l. The amount of tartaric acid formed in 16 liters of the reaction mixture was 2.94 Kg.

Gypsum ($CaSO_4.2H_2O$), 3.8 Kg, was added to the reaction mixture, and the resulting calcium tartrate slurry was thoroughly washed with water and then separated by filtration. The calcium tartrate separated was suspended in water, and equimolar sulfuric acid was added. The resulting gypsum precipitate was separated by filtration, and the precipitate was washed fully to be free from tartaric acid. The tartaric acid solution thus obtained was concentrated by heating to precipitate the remaining calcium sulfate, and the gypsum was again separated by filtration. The concentration of tartaric acid in the solution was adjusted to about 50% by weight, and the solution was decolorized with activated charcoal. The solution was successively passed through a cation-exchange resin column and an anion-exchange resin column. The purified aqueous solution of tartaric acid was concentrated by heating to afford 2.8 Kg of purified L-tartaric acid. The degree of rotation of the purified aqueous solution of tartaric acid ($[\alpha]_D^{20}$ ($C_{20}$, $H_2O$)) was found to be +12.81°. On the other hand, tartaric acid of special reagent grade commercially available had $[\alpha]_D^{20}$ ($C_{20}$, $H_2O$) of + 12.84°. The degree of rotation of tartaric acid, as found in the literature, is +12.0°.

What is claimed is:

1. A method for preparing L-tartaric acid which comprises reacting cells of a microorganism belonging to the genus Nocardia having the ability to produce an enzyme which hydrolyzes the epoxy ring of cis-epoxysuccinic acid or crude cisepoxysuccinate hydrolase derived from said microorganism with cisepoxysuccinate acid or a derivative thereof having the cis-epoxysuccinate acid structure in an aqueous medium containing at least one surfactant, and thereafter recovering L-tartaric acid from said aqueous medium.

2. A method according to claim 1 wherein said microorganism belongs to the species *Nocardia tartaricans*.

3. A method according to claim 2 wherein said microorganism is selected from the group consisting of *Nocardia Tartaricans* ATCC 31190 and *Nocardia Tartaricans* ATCC 31191.

4. A method according to claim 1 wherein said reaction step is carried out at a temperature of from about 20° C. to about 60° C.

5. A method according to claim 1 wherein said reaction step is carried out at a pH of about 6 to about 10.

6. A method according to claim 1 wherein said reaction step is carried out by culturing said microorganism in said aqueous medium.

7. A method according to claim 1 wherein said reaction step is carried out using a culture broth or a cell free extract containing said cis-epoxysuccinate hydrolase.

8. A method according to claim 1 wherein said reaction step is carried out using dried or pulverized cells of said microorganism.

9. A method according to claim 1 wherein said aqueous medium contains from 0.001% to 1% by weight of said surfactant based upon said medium.

10. The process of claim 1 wherein said surfactant is at least one member selected from the group consisting of nonionic, anionic and cationic surfactants.

11. The process of claim 10 wherein said surfactant is at least one anionic surfactant selected from the group consisting of alkyl polyoxyethylene phosphoric acid esters and higher fatty acid salts.

12. The process of claim 10 wherein said surfactant is at least one nonionic surfactant selected from the group consisting of polyoxyethylene sorbitan fatty acid esters, a polyoxyethylene/polyoxypropylene block copolymer and polyoxyethylene alkyl ethers.

13. The process of claim 10 wherein said surfactant is at least one cationic surfactant selected from the group consisting of long-chain alkyl quaternary ammonium salts and long-chain alkyl pyridinium salts.

14. A method for preparing L-tartaric acid which comprises culturing a microorganism belonging to the genus Nocardia having the ability to produce an enzyme which hydrolyzes the epoxy ring of cis-epoxysuccinic acid in an aqueous medium containing cis-epoxysuccinic acid or a derivative thereof having the cis-epoxysuccinic acid structure and from 0.001% to 1% of at least one surfactant based upon the weight of said medium until L-tartaric acid is formed in medium and thereafter recovering said L-tartaric acid.

15. A method according to claim 14 wherein said microorganism is selected from the group consisting of Nocardia tartaricans ATCC 31190 and Nocardia tartaricans nov. sp. ATCC 31191.

* * * * *

UNITED STATES PATENT OFFICE
CERTIFICATE OF CORRECTION

Patent No. 4,017,362    Dated April 12, 1977

Inventor(s) YUICHI MIURA, et al.    Page 1 of 2

It is certified that error appears in the above-identified patent and that said Letters Patent are hereby corrected as shown below:

On the Cover Page, add:

[30] FOREIGN APPLICATION PRIORITY DATA

Oct. 9, 1975    Japan    50-121313

Col. 1, line 43, "eso" should be --meso--;

Col. 2, line 57, "reacton" should be --reaction--;

Col. 4, line 36, "(30)" should be --(+)--;

Col. 5, line 2, delete "fastness";

line 9, "utilizatin" should be --utilization--;

line 19, "reducton" should be --reduction--;

Col. 7, line 39, "strai" should be --strain--;

line 55, "sutable" should be --suitable--;

Col. 10, line 36, "sutable" should be --suitable--;

Col. 18, line 54, before "medium" add --said--;

UNITED STATES PATENT OFFICE
CERTIFICATE OF CORRECTION

Patent No. 4,017,362        Dated April 12, 1977

Inventor(s) YUICHI MIURA, et al.        Page 2 of 2

It is certified that error appears in the above-identified patent and that said Letters Patent are hereby corrected as shown below:

Col. 18, line 58, delete "nov. sp."

Signed and Sealed this ninth Day of August 1977

[SEAL]

Attest:

RUTH C. MASON  
Attesting Officer

C. MARSHALL DANN  
Commissioner of Patents and Trademarks